(12) United States Patent
Lee et al.

(10) Patent No.: US 8,309,740 B2
(45) Date of Patent: Nov. 13, 2012

(54) ONE-POT SYNTHESIS OF FLUORINATED IONIC LIQUIDS

(75) Inventors: Hyun Joo Lee, Seoul (KR); Dong Jin Suh, Seoul (KR); Byoung Sung Ahn, Seoul (KR); Hong Gon Kim, Seoul (KR); Chang Soo Kim, Daegu (KR); Hoon Sik Kim, Seongbuk-gu (KR)

(73) Assignee: Korea Institute of Science and Technology, Seoul (KR)

( * ) Notice: Subject to any disclaimer, the term of this patent is extended or adjusted under 35 U.S.C. 154(b) by 1010 days.

(21) Appl. No.: 12/192,433

(22) Filed: Aug. 15, 2008

(65) Prior Publication Data
US 2009/0286976 A1    Nov. 19, 2009

(30) Foreign Application Priority Data

May 13, 2008   (KR) ................. 10-2008-0044190

(51) Int. Cl.
| | |
|---|---|
| C07D 207/02 | (2006.01) |
| C07D 211/04 | (2006.01) |
| C07D 213/06 | (2006.01) |
| C07D 233/06 | (2006.01) |
| C07D 233/56 | (2006.01) |
| C07D 237/06 | (2006.01) |
| C07D 239/24 | (2006.01) |
| C07D 241/04 | (2006.01) |
| C07D 249/02 | (2006.01) |
| C07D 251/56 | (2006.01) |
| C07D 253/06 | (2006.01) |
| C07D 295/02 | (2006.01) |

(52) U.S. Cl. ............... 548/343.1; 548/255; 548/376.1; 548/579; 564/296; 544/158; 544/180; 544/182; 544/215; 544/224; 544/229; 544/358

(58) Field of Classification Search ............. 548/343.1, 548/255, 376.1, 579; 564/296; 544/158, 544/182, 215, 224, 229, 358
See application file for complete search history.

(56) References Cited

U.S. PATENT DOCUMENTS

2010/0222598 A1*  9/2010  Komatsu et al. ........... 548/343.1

OTHER PUBLICATIONS

Xue, Hong et al.: "Ionic Liquids with Fluorine-Containing Cations", *Eur. J. Inorg. Chem.*, 2005, pp. 2573-2580.
Bonhote, Pierre et al.: "Hydrophobic, Highly Conductive Ambient-Temperature Molten Salts", *Inorg. Chem.*, 1996, 35, pp. 1168-1178.
Yagupolskii, Yurii L. et al.: "Novel Ionic Liquids-Imidazolium salts with a difluoromethylene fragment directly bonded to the nitrogen atom", *Journal of Fluorine Chemistry*, 126 (2005), pp. 669-672.
Rudyuk, Vitalij V. et al.: "N-Polyfluoroethyl and N-2-chlorodifluorovinyl derivatives of azoles", *Journal of Fluorine Chemistry* 125 (2004) pp. 1465-1471.
Zhang et al, "Direct methylation and trifluoroethylation of imidazole and pyridine derivatives" Chem. Commun., 2003, pp. 2334-2335.
Lee et al. "Alkyl-fluoroalkylimidazolium-Based Ionic Liquids as Efficient CO2 Absorbents" Energy Fuels, 2010, 24, pp. 6689-6692.
Kim et al. "Facile One-Pot Synthesis of 1-Alkyl-3-polyfluoroalkyl Imidazolium Ionic Liquids" SYNLETT, 2009, 13, pp. 2101-2104.x.

* cited by examiner

*Primary Examiner* — Venkataraman Balasubramanian
(74) *Attorney, Agent, or Firm* — Frommer Lawrence & Haug LLP; Ronald R. Santucci

(57) ABSTRACT

The present invention relates to a method for one-pot synthesis of ionic liquid with fluoroalkyl group, more particularly to a method for one-pot synthesis of ionic liquid with fluoroalkyl group represented by the following Chemical Formula 1 by adding and reacting a nitrogen-containing compound, a Brønsted acid of the formula YH and a fluoroolefin compound of the formula $CFR^1{=}CR^2R^3$ in a single reactor:

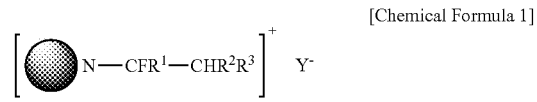

[Chemical Formula 1]

wherein

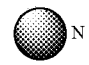

represents a nitrogen-containing compound; $Y^-$ represents an anion of the Brønsted acid; and $R^1$, $R^2$ and $R^3$, which may be same or different, represent hydrogen, fluorine, $C_1$-$C_{10}$ alkyl or $C_1$-$C_{10}$ fluoroalkyl having from 1 to 23 fluorine atoms.

6 Claims, No Drawings

ONE-POT SYNTHESIS OF FLUORINATED IONIC LIQUIDS

CROSS-REFERENCE TO RELATED APPLICATION

This application claims under 35 U.S.C. §119(a) the benefit of Korean Patent Application No. 10-2008-0044190 filed May 13, 2008, the entire contents of which are incorporated herein by reference.

BACKGROUND

1. Technical Field

The present invention relates to a method for one-pot synthesis of ionic liquid with fluoroalkyl group, more particularly to a method for one-pot synthesis of ionic liquid with fluoroalkyl group represented by the following Chemical Formula 1 by adding and reacting a nitrogen-containing compound, a Brønsted acid of the formula YH and a fluoroolefin compound of the formula $CFR^1=CR^2R^3$ in a single reactor:

[Chemical Formula 1]

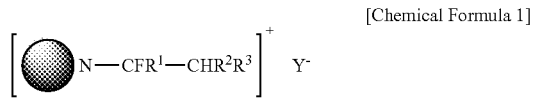

wherein

represents a nitrogen-containing compound; $Y^-$ represents an anion of the Brønsted acid; and $R^1$, $R^2$ and $R^3$, which may be same or different, represent hydrogen, fluorine, $C_1$-$C_{10}$ alkyl or $C_1$-$C_{10}$ fluoroalkyl having from 1 to 23 fluorine atoms.

2. Background Art

An ionic liquid is a salt compound consisting of an organic cation and an anion. While salt compounds melt at relatively high temperature of 800° C. or above in general, ionic liquids exist as liquid even at relatively low temperature of 100° C. or below. In general, an ionic liquid is non-volatile, not-toxic, non-flammable and thermally stable, and has a good ion conductivity. Therefore, it is applied to various chemical areas, including a green solvent, a solvent for a catalyst, a separation medium or electrolyte, a solvent for hardly soluble materials such as cellulose, a storage medium for a toxic gas, or the like. Further, because the physical and chemical properties of ionic liquids can be tuned by changing the structure of the cation and the anion constituting the ionic liquid, an ionic liquid that is optimized for a particular application can be synthesized easily. Thus, it is commonly called as "designer solvent." Typical examples of the ionic liquid are compounds consisting of a nitrogen-containing cation and an anion such as halogen like $Cl^-$, $Br^-$ and $I^-$, $BF_4^-$, $PF_6^-$, $(CF_3SO)_2N^-$, $CF_3SO_3^-$, $MeSO_3^-$, $NO_3^-$, $CF_3CO_2^-$, $CH_3CO_2^-$, etc. The nitrogen-containing cation constituting an ionic liquid may be quaternary ammonium, pyrrolidium, pyrrolium, imidazolium, pyrazolium, triazolium, pyridinium, pyridazinium, pyrimidinium, and the like.

The most common method of preparing an ionic liquid [*Inorg. Chem.* 1996, 35, 1168] is to react an imidazole compound with an alkyl halide ($R_2$—X) to prepare an ionic compound, imidazolium halide, and then exchange the anion with a wanted anion ($Y^-$) using a metal salt (MY) containing the anion, as shown in the following Scheme 1.

[Scheme 1]

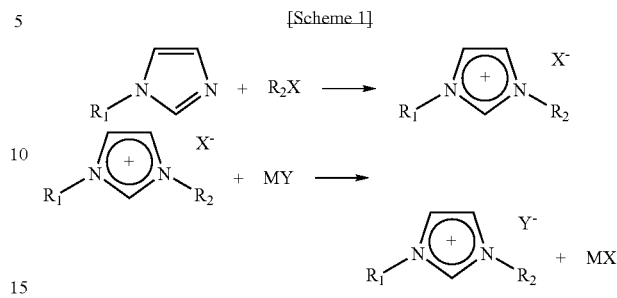

In Scheme 1, $R_1$ and $R_2$ independently represents hydrogen or alkyl; X represents halogen; M represents alkali metal; and Y represents $Cl^-$, $Br^-$, $I^-$, $BF_4^-$, $PF_6^-$, $(CF_3SO)_2N^-$, $CF_3SO_3^-$, $CH_3SO_3^-$, $NO_2^-$, $NO_3^-$, $CF_3CO_2^-$ or $CH_3CO_2^-$.

The preparation method according to Scheme 1 consists of at least two steps, excluding the step of preparing the halogen anion containing compound. In addition, a step of removing the reaction byproduct, metal halide (MX), is required. Further, because the final product, the ionic liquid, dissolves the metal halide, it is almost impossible to completely remove the metal halide.

Recently, ionic liquid with fluoroalkyl group bonded to nitrogen-containing cation, as represented by Chemical Formula 1, has been developed. The ionic liquid with fluoroalkyl group represented by Chemical Formula 1 has many fluorine atoms in the molecule. Because fluorine is the most electronegative element, the liquid has distinct physical and chemical properties, including solubility and potential window, which is different from those of ionic liquids with hydrocarbon-based alkyl group. The ionic liquid with fluoroalkyl group represented by Chemical Formula 1 can be prepared by the multi-step process as described in Scheme 1. That is, after reacting imidazole with fluoroalkyl halide to obtain imidazolium halide with fluoroalkyl group, the wanted ionic liquid with fluoroalkyl group can be attained by exchanging the anion using a metal salt (MY) containing $Y^-$ anion.

However, as mentioned above, this preparation method is composed of two or more steps in order to obtain the ionic liquid with fluoroalkyl group, and requires the process for removing the reaction byproduct metal halide (MX). Further, because the final product, which is an ionic liquid, dissolves the metal halide, it is almost impossible to completely remove the metal halide. Besides, highly reactive fluoroalkyl iodide, which is used as alkylation reagent, is expensive and discolored easily upon exposure to air or light. This affects the color of the final product.

Recently, a method of synthesizing 1-(1,1,2,2-tetrafluoroethyl)imidazole by reacting a fluoroolefin compound such as tetrafluoroethylene ($CF_2=CF_2$) with imidazole has been proposed [WO 2007/074632; *J. Fluorine Chem.* 125 (2004) 1465; *J. Fluorine Chem.* 126 (2005) 669]. However, this method requires a further alkylation, and anion exchange step to introduce anions other than halide.

DISCLOSURE OF THE INVENTION

[Technical Problem]

The present invention has been made in view of the above problems, and it is an object of the present invention to provide a method for one-pot synthesis of ionic liquid with fluoroalkyl group.

The preparation method according to the present invention is advantageous over general preparation methods in that ionic liquid with fluoroalkyl group can be synthesized directly in relatively short time in a single reactor.

[Technical Solution]

In an aspect, the present invention provides a method for one-pot synthesis of ionic liquid with fluoroalkyl group represented by the following Chemical Formula 1 by reacting a nitrogen-containing compound, a Brønsted acid of the formula YH and a fluoroolefin compound of the formula $CFR^1=CR^2R^3$ in a single reactor:

[Chemical Formula 1]

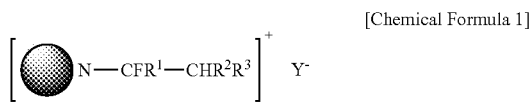

wherein

represents a nitrogen-containing compound, which is an amine compound or a five- or six-membered heterocyclic compound having from 1 to 3 nitrogen atoms, and may be substituted by a substituent selected from $C_1$-$C_{10}$ alkyl, haloalkyl having from 1 to 23 halogen atoms, $C_2$-$C_{10}$ alkenyl and $C_2$-$C_{10}$ alkynyl or unsubstituted; $R^1$, $R^2$ and $R^3$, which may be same or different, represent hydrogen, fluorine, $C_1$-$C_{10}$ alkyl or $C_1$-$C_{10}$ fluoroalkyl having from 1 to 23 fluorine atoms; and $Y^-$ represents $Cl^-$, $Br^-$, $I^-$, $BF_4^-$, $PF_6^-$, $(CF_3SO)_2N^-$, $CF_3SO_3^-$, $CH_3SO_3^-$, $NO_2^-$, $NO_3^-$, $CF_3CO_2^-$ or $CH_3CO_2^-$.

[Best Mode]

The conventional preparation method of ionic liquid with fluoroalkyl group involves a multi-step process including fluoroalkyl and anion exchange, and requires an additional purification process for removing the anion exchange byproduct metal halide. In contrast, the present invention provides a method for preparing ionic liquid with fluoroalkyl group through one-pot reaction by adding all the reactants in a single reactor. Further, the purification is simple because metal halide is not formed as byproduct.

In the preparation method according to the present invention, reaction temperature is maintained at between 0° C. and 100° C., preferably between 20° C. and 80° C., particularly preferably at around room temperature, that is between 20° C. and 30° C. When the reaction temperature is below 0° C., reaction rate decreases. And, when the reaction temperature exceeds 100° C., the fluoroolefin compound may polymerize or the amine reactant could be decomposed.

For the reaction solvent, any inert solvent that does not affect the reaction may be used. Specific examples of the solvent that may be used in the preparation method according to the present invention include $C_2$-$C_{10}$ nitriles including acetonitrile, $C_2$-$C_{10}$ ketones including acetone, $C_3$-$C_{10}$ amides including dimethylformamide, $C_6$-$C_{20}$ aromatic hydrocarbons including toluene, $C_6$-$C_{20}$ aromatic halogenated hydrocarbons including chlorobenzene, $C_1$-$C_{10}$ aliphatic halogenated hydrocarbons including dichloromethane, and $C_1$-$C_{10}$ alcohols including methanol. The solvent may be used in an amount of 0.5 to 20 weight equivalents, preferably 1 to 10 weight equivalents, based on the weight of the nitrogen-containing compound represented by Chemical Formula 1.

The nitrogen-containing compound represented by Chemical Formula 1, which is used as a starting material in the preparation method according to the present invention, may be an amine compound or a five- or six-membered heterocyclic compound containing from 1 to 3 nitrogen atoms. The heterocyclic compound may be a five-membered heterocyclic compound such as pyrrolidine, pyrrole, imidazole, 4,5-dihydroimidazole, triazole, 4,5-dihydrotriazole, or a six-membered heterocyclic compound such as morpholine, piperidine, piperazine, pyridine, pyridazine and triazine. If necessary, the nitrogen-containing compound may be substituted by at least one substituent selected from $C_1$-$C_{10}$ alkyl, $C_1$-$C_{10}$ haloalkyl having from 1 to 23 halogen atoms, $C_2$-$C_{10}$ alkenyl and $C_2$-$C_{10}$ alkynyl or unsubstituted. Preferably, the substituent in the nitrogen-containing compound may be selected from $C_1$-$C_6$ alkyl, $C_1$-$C_6$ haloalkyl having from 1 to 23 halogen atoms, $C_2$-$C_6$ alkenyl and $C_2$-$C_6$ alkynyl. Specific examples of the substituent in the nitrogen-containing compound may include methyl, ethyl, propyl, butyl, chloromethyl, trifluoromethyl, 1,1-dichloroethyl, 1,2-dichloroethyl, 3,3,3-trifluoropropyl, vinyl, allyl, propenyl, butenyl, and the like.

The Brønsted acid, which is used as a starting material in the preparation method according to the present invention, is an acid compound having $Y^-$ anion. Specific examples of the Brønsted acid may include HCl, HBr, HI, $HBF_4$, $HPF_6$, $(CF_3SO)_2NH$, $CF_3SO_3H$, $CH_3SO_3H$, $HNO_2$, $HNO_3$, $CF_3CO_2H$, $CH_3CO_2H$, and the like. In the preparation method according to the present invention, the Brønsted acid may be used in an amount of 1 to 3 molar equivalents based on 1 mol of the nitrogen-containing compound represented by Chemical Formula 1. When the Brønsted acid is used in an amount less than 1 molar equivalent, final yield decreases because unreacted nitrogen-containing compound remains. And, when the Brønsted acid is used in an amount exceeding 3 molar equivalents, a further purification process for removing the excessive acid could be required.

The fluoroolefin compound, which is used as a starting material in the preparation method according to the present invention, may be represented by the formula $CFR^1=CR^2R^3$, Specific examples of the fluoroolefin compound may include $CHF=CH_2$, $CHF=CHF$, $CF_2=CH_2$, $CF_2=CHF$, $CF_2=CF_2$, $CHF=CFCF_3$, $CF_2=CFCF_3$, $CF_2=CFCF_2CF_3$, and the like. In the preparation method according to the present invention, the fluoroolefin compound may be used in an amount of 1 to 5 molar equivalents, preferably 1 to 2 molar equivalents, based on 1 mol of the nitrogen-containing compound represented by Chemical Formula 1. When the fluoroolefin compound is used in an amount less than 1 molar equivalent, yield of the target compound may decrease. However, even when the fluoroolefin compound is used in an amount exceeding 5 molar equivalents, yield does not increase further.

[Mode for Invention]

The following examples illustrate the present invention in further detail. However, they are not intended to limit the same.

EXAMPLE 1

1-Methylimidazole (10 mmol) was dissolved in acetonitrile (20 mL) in a 100 mL high pressure reactor, and HCl (ether solution, 10 mmol) was added slowly. After sealing the reactor and removing air, 1,1,2,3,3,3-hexafluoropropylene (20 mmol) was added and stirring was carried out at room temperature (20° C.) for 2 hours. Pressure inside the reactor, which was initially maintained at room temperature at about 60 psig by 1,1,2,3,3,3-hexafluoropropylene, decreased as the reaction occurred. When the pressure did not decrease any more, reaction product was taken from the reactor and the solvent was removed under reduced pressure. The reaction product 1-methyl-3-(1,1,2,3,3,3-hexafluoropropyl)imidazolium chloride was obtained as white solid. Yield of the obtained ionic liquid was calculated by the following Equation 1.

Yield 97%; $^1$H NMR (300 MHz, DMSO-$d_6$, 25° C., ppm) δ 9.55 (s, 1H, CH-Im), 7.81, 7.58 (d, 2H, CH-Im), 5.99 (m, 1H, CHF), 3.86 (s, 3H, CH$_3$).

$$\text{Yield}(\%) = \frac{\text{Amount of produced ionic liquid (mmol)}}{\text{Amount of used nitrogen-containing compound (mmol)}} \times 100 \quad \text{[Equation 1]}$$

EXAMPLE 2

Ionic liquid was prepared in the same manner as in Example 1, except for varying the nitrogen-containing compound, the Brønsted acid and the fluoroolefin compound as listed in the following Table 1. Yield of the obtained ionic liquid was calculated by the Equation 1 and is given in Table 1.

TABLE 1

| Nitrogen-containing compound | Brønsted acid | Fluoroolefin compound | Produced ionic liquid | Yield (%) |
|---|---|---|---|---|
| Et$_3$N | CF$_3$CO$_2$H | CF$_3$—CF=CF$_2$ | [Et$_3$N—CF$_2$CFHCF$_3$]$^+$CF$_3$CO$_2^-$ | 95 |
| Et$_2$HN | CH$_3$CO$_2$H | CF$_3$—CF=CF$_2$ | [Et$_2$HN—CF$_2$CFHCF$_3$]$^+$CH$_3$CO$_2^-$ | 92 |
| EtH$_2$N | HCl | CF$_3$—CF=CF$_2$ | [EtH$_2$N—CF$_2$CFHCF$_3$]$^+$Cl$^-$ | 93 |
| 1-vinylimidazole | HPF$_6$ | CF$_3$—CF=CF$_2$ | 1-vinyl-3-(CF$_2$CFHCF$_3$)imidazolium PF$_6^-$ | 96 |
| 1-propylpyrrolidine | HBF$_4$ | CF$_3$—CF=CF$_2$ | 1-propyl-1-(CF$_2$CFHCF$_3$)pyrrolidinium BF$_4^-$ | 96 |
| N-methylmorpholine | CF$_3$SO$_3$H | CF$_3$—CF=CF$_2$ | N-methyl-N-(CF$_2$CFHCF$_3$)morpholinium CF$_3$SO$_3^-$ | 87 |
| pyridine | CH$_3$SO$_3$H | CF$_3$—CF=CF$_2$ | 1-(CF$_2$CFHCF$_3$)pyridinium CH$_3$SO$_3^-$ | 89 |
| 2-methyl-2-imidazoline | (CF$_3$SO)$_2$NH | CF$_3$CF$_2$—CF=CF$_2$ | 2-methyl-1-(CF$_2$CHFCF$_2$CF$_3$)-2-imidazolinium (CF$_3$SO)$_2$N$^-$ | 83 |

TABLE 1-continued

| Nitrogen-containing compound | Brønsted acid | Fluoroolefin compound | Produced ionic liquid | Yield (%) |
|---|---|---|---|---|
| 4-methyl-5-(hydroxymethyl)-1H-pyrazole | HNO$_3$ | CF$_3$CF$_2$—CF=CF$_2$ | [4-methyl-5-(hydroxymethyl)-1-(CF$_2$CHFCF$_2$CF$_3$)-1H-pyrazolium]$^+$ NO$_3^-$ | 91 |
| 4,5-dihydro-1H-1,2,3-triazole | HNO$_2$ | CH$_2$=CF$_2$ | [1-(CF$_2$CH$_3$)-4,5-dihydro-1H-1,2,3-triazolium]$^+$ NO$_2^-$ | 75 |
| 5-(2-butenyl)-1H-1,2,3-triazole | CF$_3$CO$_2$H | CH$_2$=CF$_2$ | [5-(2-butenyl)-1-(CF$_2$CH$_3$)-1H-1,2,3-triazolium]$^+$ CF$_3$CO$_2^-$ | 76 |
| 1-(trifluoromethyl)piperidine | CH$_3$CO$_2$H | CF$_3$—CF=CF$_2$ | [1-(CF$_2$CHFCF$_3$)-1-(CF$_3$)-piperidinium]$^+$ CH$_3$CO$_2^-$ | 94 |
| 1-ethyl-4-methylpiperazine | HCl | CF$_2$=CF$_2$ | [1-ethyl-4-methyl-4-(CF$_2$CHF$_2$)-piperazinium]$^+$ Cl$^-$ | 93 |
| pyridazine | HPF$_6$ | CF$_3$—CF=CF$_2$ | [1-(CF$_2$CHFCF$_3$)-pyridazinium]$^+$ PF$_6^-$ | 91 |
| pyrimidine | HBF$_4$ | CF$_2$=CF$_2$ | [1-(CF$_2$CHF$_2$)-pyrimidinium]$^+$ BF$_4^-$ | 92 |
| 1,3,5-triazine | CF$_3$SO$_3$H | CF$_3$—CF=CF$_2$ | [1-(CF$_2$CHFCF$_3$)-1,3,5-triazinium]$^+$ CF$_3$SO$_3^-$ | 92 |
| 1,2,4-triazine | CH$_3$SO$_3$H | CF$_2$=CF$_2$ | [1-(CF$_2$CHF$_2$)-1,2,4-triazinium]$^+$ CH$_3$SO$_3^-$ | 95 |

EXAMPLE 3

Ionic liquid was prepared in the same manner as in Example 1, except for varying reaction temperature as listed in the following Table 2. Yield of the obtained ionic liquid was calculated by the Equation 1 and is given in Table 2.

TABLE 2

| Nitrogen-containing compound | Brønsted acid | Fluoroolefin compound | Produced ionic liquid | Reaction Temperature | Yield (%) |
|---|---|---|---|---|---|
| 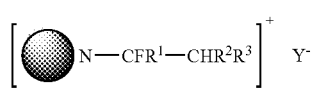 | $CF_3CO_2H$ | $CF_3$—$CF$=$CF_2$ |  $BF_4^-$ | 0° C. | 35 |
| | | | | 20° C. | 97 |
| | | | | 30° C. | 97 |
| | | | | 50° C. | 96 |
| | | | | 80° C. | 95 |
| | | | | 100° C. | 93 |

[Industrial Applicability]

As described above, the present invention relates to a preparation method for one-pot synthesis of ionic liquid with fluoroalkyl group in short time with good yield, by adding the starting materials nitrogen-containing compound, Brønsted acid having $Y^-$ anion, and fluoroolefin compound in a single reactor. It is possible in the present invention to perform the reaction over a wide temperature range of from 0° C. to 100° C., particularly even at low temperature around room temperature. Especially, as the metal halide produced as a byproduct in the conventional preparation method is prevented, the process is simplified significantly because the separation and purification can be carried out easily.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A preparation method for one-pot synthesis of ionic liquid with fluoroalkyl group represented by the following Chemical Formula 1 by reacting a nitrogen-containing compound with a Brønsted acid of the formula YH, and followed by reacting with a fluoroolefin compound of the formula $CFR^1$=$CR^2R^3$ in a single reactor, wherein no metal halide byproduct is formed and no anion exchange step is carried out:

[Chemical Formula 1]

$$\left[ \bigcirc N—CFR^1—CHR^2R^3 \right]^+ Y^-$$

wherein

represents a nitrogen-containing compound as a tertiary amine, which is a five- or six-membered heterocyclic compound having from 1 to 3 nitrogen atoms, and optionally substituted by a substituent selected from C1-C10 alkyl, C1-C4 alkyl having from 1 to 8 halogen atoms, C2-C10 alkenyl and C2-C10 alkynyl or unsubstituted;

$R^1$, $R^2$ and $R^3$, which may be same or different, represent hydrogen, fluorine, C1-C10 alkyl or C1-C10 fluoroalkyl having from 1 to 8 fluorine atoms; and Y represents, BF4, PF6, (CF3SO)2N, NO2, NO3, CF3CO2 or CH3CO2.

2. The preparation method as set forth in claim 1, wherein the nitro-containing compound as a tertiary amine is a heterocyclic compound selected from pyrrolidine, pyrrole, imidazole, 4,5-dihydroimidazole, triazole, 4,5-dihydrotriazole, morpholine, piperidinc, piperazine, pyridine, pyridazine and triazine, and the heterocyclic compound optionally substituted by at least one substituent selected from C1-C6 alkyl, C1-C6 haloalkyl having from 1 to 8 halogen atoms, C2-C6 alkenyl and C2-C6 alkynyl or unsubstituted.

3. The preparation method as set forth in claim 1, wherein the Brønsted acid is selected from, HBF4, HPF6, (CF3SO)2NH, HNO2, HNO3, CF3CO2H and CH3CO2H, and is used in an amount of 1 to 3 molar equivalents based on 1 mol of the nitrogen-containing compound represented by

4. The preparation method as set forth in claim 1, wherein the fluoroolefin compound is selected from CHF=CH2, CHF=CHF, CF2=CH2, CF2=CHF, CF2=CF2, CHF=CFCF3, CF2=CFCF3 and CF2=CFCF2CF3, and is used in an amount of 1 to 2 molar equivalents based on 1 mol of the nitrogen-containing compound represented by 5. The preparation method as set forth in claim 1, wherein the reaction is performed at 0° C. to 100° C.

6. The preparation method as set forth in claim 2, wherein the reaction is performed at 0° C. to 100° C.

* * * * *